US009108173B2

(12) United States Patent
Lee et al.

(10) Patent No.: US 9,108,173 B2
(45) Date of Patent: Aug. 18, 2015

(54) DROPLET-GENERATING METHOD AND DEVICE

(71) Applicant: NATIONAL CHENG KUNG UNIVERSITY, Tainan (TW)

(72) Inventors: Denz Lee, Tainan (TW); Chin-Yao Chen, Tainan (TW)

(73) Assignee: NATIONAL CHENG KUNG UNIVERSITY (TW)

( * ) Notice: Subject to any disclaimer, the term of this patent is extended or adjusted under 35 U.S.C. 154(b) by 113 days.

(21) Appl. No.: 13/930,297

(22) Filed: Jun. 28, 2013

(65) Prior Publication Data

US 2014/0161685 A1 Jun. 12, 2014

(30) Foreign Application Priority Data

Dec. 7, 2012 (TW) ............................ 101146230 A

(51) Int. Cl.
*G01N 15/06* (2006.01)
*G01N 33/00* (2006.01)
*G01N 33/48* (2006.01)
*B01F 13/00* (2006.01)
*B01F 3/08* (2006.01)

(52) U.S. Cl.
CPC ........... *B01F 13/0069* (2013.01); *B01F 3/0807* (2013.01); *B01F 13/0062* (2013.01)

(58) Field of Classification Search
USPC ......... 422/502, 503, 504, 505, 508, 509, 521; 436/43, 180
See application file for complete search history.

(56) References Cited

U.S. PATENT DOCUMENTS

| | | | | |
|---|---|---|---|---|
| 6,062,261 | A * | 5/2000 | Jacobson et al. | 137/827 |
| 6,120,666 | A * | 9/2000 | Jacobson et al. | 204/452 |
| 6,783,647 | B2 * | 8/2004 | Culbertson et al. | 204/453 |
| 2010/0126862 | A1 * | 5/2010 | Sabin et al. | 204/457 |

OTHER PUBLICATIONS

Office Action issued in corresponding Taiwanese Patent Application No. 10420089660 on Jan. 22, 2015, consisting of 8 pp.
Perkins, Sasha. "Three-Dimensional Flow-Focusing in Microfluidic Device", The 2007 NNIN REU Research Accomplishments, National Nanotechnology Infrastructure Network, 2007. pp. 22-23 and Figs. 1-3.
Chang, Chih-Chang et al. "Three-dimensional hydrodynamic focusing in two-layer polydimethylsiloxane (PDMS) microchannels", Journal of Micromechanics and Microengineering, Jun. 29, 2007. pp. 1480-1481 and Figs. 1-3.
Hong, Sungmin et al. "Microfluidic three-dimensional hydrodynamic flow focusing for the rapid protein concentration analysis", Biomicrofluidics, [online] Jun. 20, 2012.

* cited by examiner

*Primary Examiner* — Brian J Sines
(74) *Attorney, Agent, or Firm* — Volpe and Koenig, P.C.

(57) ABSTRACT

A droplet-generating device is provided. The droplet-generating device comprises a first microchannel and a second microchannel. The first microchannel includes a first fluid inlet and a second fluid inlet. The second microchannel crossing over and communicating with the first microchannel at an intersectional region includes a third fluid inlet, a fourth fluid inlet, a fluid outlet, a three-way junction and a side wall. The intersectional region is configured between the third fluid inlet and the three-way junction, and the side wall is disposed between the fourth fluid inlet and the fluid outlet and extended downward. A method of producing a droplet is also provided.

9 Claims, 8 Drawing Sheets

DROPLET-GENERATING METHOD AND DEVICE

FIELD OF INVENTION

The present disclosure relates to a technology of generating droplets, especially to a technology of generating micro-droplets by using a three-dimensional (3D) device.

BACKGROUND

In recent years, the researches as to introduce a fluid into microchannels for conducting the chemical reaction or generating microparticles are interested. Further, the development of the semiconductor manufacturing technologies, which are the gradually mature technologies, also facilitates the fabrication of the miniaturized fluid field channels and indirectly promotes the development of this filed. In the microfluidic chip, the application and control of the fluid play an important role in achieving the detecting purpose. The multiphase flows in the microfluidic chip, based on the differences in the geometrical shape or the subjected force, could make the continuous microdroplet emulsion formation have the applicable property that there is no interference among the phase interfaces. Therefore, the microfluidic chip is usually used in the fields of various chemical syntheses, biomedical detection, drug delivery, and so on.

Currently, most microchannels used in the microfluidic chip for generating microdroplets are two-dimensional (2D) channels. The structure of the microfluidic chip is more and more complex in response to the diversity of the problems to be solved. However, the repeatability and reliability of the data derived from the microfluidic chip decrease with the increased complexity of the channel structure design. For integrating more functions into the limited area on the chip, there is the need of simple channel structures with the simplicity in the fabrication and the practicality in the application for solving the problems that previously has to be solved by the complex structures.

In addition, in the known 2D cross channels made of poly (dimethylsiloxane) (PDMS), the process of generating the water droplet by using the oil as the continuous phase is easier owing to the hydrophobic property of the PDMS. In contrast, if the oil is used as the dispersed phase, the process of generating the oil droplet is hard due to the viscosity of the oil and the contacting angle with the channel wall.

For overcoming the mentioned problems, the novel droplet-generating method and device are provided in the present disclosure after a lot of researches, analyses and experiments by the inventors.

SUMMARY

In accordance with one aspect of the present disclosure, a droplet-generating device is provided. The droplet-generating device comprises a first microchannel and a second microchannel. The first microchannel includes a first fluid inlet and a second fluid inlet. The second microchannel crossing over and communicating with the first microchannel at an intersectional region includes a third fluid inlet, a fourth fluid inlet, a fluid outlet, a three-way junction and a side wall. The intersectional region is configured between the third fluid inlet and the three-way junction, and the side wall is disposed between the fourth fluid inlet and the fluid outlet and extended downward.

In accordance with another aspect of the present disclosure, a droplet-generating device is provided. The droplet-generating device comprises a first channel and a second channel crossing over and communicating with the first channel. The first channel includes a first inlet and a second inlet. The second channel includes a third inlet and a first outlet. The droplet-generating device further comprises a falling structure connected with the first outlet.

In accordance with one more aspect of the present disclosure, a method of producing a droplet is provided. The method comprises steps of providing a first channel including a first inlet and a second inlet, providing a second channel crossing over and communicating with the first channel, and providing a falling structure. The second channel includes a third inlet and an outlet. The falling structure is connected to the outlet. The method further comprises steps of introducing a first flowing material through the first inlet into the first channel and introducing a second flowing material through the second inlet and the third inlet into the first channel and the second channel respectively so as to produce the droplet at the falling structure.

The present disclosure may best be understood through the following descriptions with reference to the accompanying drawings, in which:

DETAILED DESCRIPTION OF THE PREFERRED EMBODIMENTS

Figure 1:
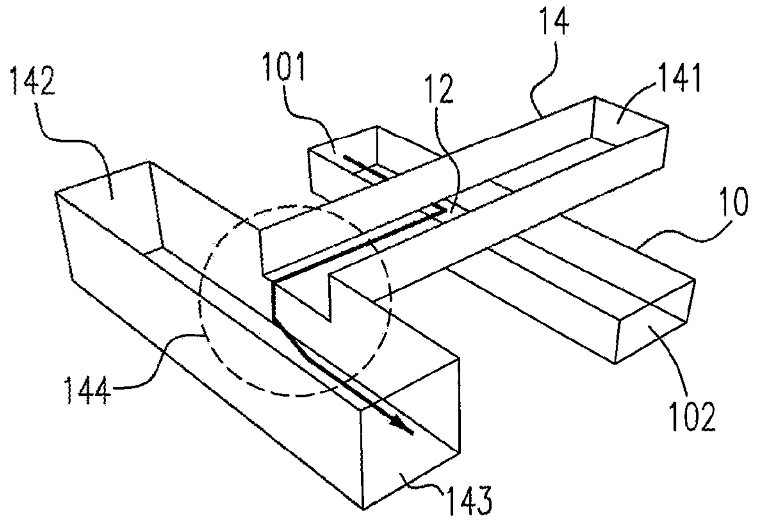
FIG. 1 shows a droplet-generating device according to a first preferred embodiment of the present disclosure.

The present invention will be described with respect to particular embodiments and with reference to certain drawings, but the invention is not limited thereto but is only limited by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments may be practiced without these specific details. In other instances, well-known methods, structures and techniques have not been shown in detail in order not to obscure an understanding of this description.

The invention will now be described by a detailed description of several embodiments. It is clear that other embodiments can be configured according to the knowledge of persons skilled in the art without departing from the true technical teaching of the present disclosure, the claimed invention being limited only by the terms of the appended claims.

Please refer to FIG. 1, which is a diagram showing a droplet-generating device according to a first preferred embodiment of the present disclosure. As shown, the droplet-generating device comprises tangential microchannels superimposed and crossing each other. The droplet-generating device may includes a first microchannel 10 and a second microchannel 14 superimposed on the first microchannel 10 to form an intersection region 12, through which the first microchannel 10 is in communication with the second microchannel 14. Via the cross superimposition of the two microchannels 10 and 14, a three-dimensional flow-focusing field is generated. The second microchannel 14, which could have a T-shape, a Y-shape or other similar shapes, is superimposed on and crossing the first microchannel 10 at a perpendicular angle or other suitable angles. In this embodiment, the width, height and aspect ration AR (=h/w, h is the height and w is the width of microchannel) of each of the first microchannel 10 and the second microchannel 14 are 100 μm, 45 μm and 0.45, respectively, but the size is not limited thereto. The first microchannel 10 includes a first fluid inlet 101 and a second fluid inlet 102. The second microchannel 14 includes a third fluid inlet 141, a fourth fluid inlet 142, a fluid outlet 143 and a three-way junction 144. The intersection region 12 lies between the third fluid inlet 141 and the three-way junction 144, and the sidewall of the second microchannel 14 between the fourth fluid inlet 142 and the fluid outlet 143 extends downward such that the second microchannel 14 has an increased height and thus a falling structure formed at the three-way junction 144. A one-fold increase in the height is preferred. Namely, the height is increased from 45 μm to 90 μm (with an AR value increased to 0.9). The height of the falling structure may be the difference of the two heights of the second microchannel. The sidewall of the second microchannel between the fourth fluid inlet and the outlet is extended downward such that a fluid falls at the three-way junction and results in a droplet.

Hereinafter an exemplary manner of generating the droplets by using the first preferred embodiment is described. Referring to FIG. 1, the arrowhead denotes the flowing direction of the dispersed phase fluid. When the dispersed phase fluid, such as oil, is brought into the first fluid inlet 101 at a flow rate of 0.001-0.015 ml/hr, and a continuous phase fluid, such as water, is brought into the second, the third and the fourth fluid inlets 102, 141 and 142 at a total flow quantity of 0.27-16.5 ml/hr, the oil would through the intersection region 12 flow from the first microchannel 10 to the second microchannel 14, and falls at the falling structure of the three-way junction 144. The formation of droplets with tunable sizes depends on the shearing force applied by the continuous phase to the dispersed phase. This shearing force deforms the interface between the two fluids until the formation of a droplet. The water introduced into the fourth fluid inlet 142 could against the fluid property of the attachment to the wall and break the falling oil, and therefore the oil droplets dispersed in water would be formed in the center of the second microchannel 14. Further, the water could prevent the formed droplets, such as the oil droplets, from attaching to the wall again. The size of the microparticles could be adjusted by controlling the flow rates of the dispersed phase and the continuous phase.

It should be noted that the first fluid inlet 101 and the fourth fluid inlet 142 are preferred at the same side of the device. That is to say, the exchange of the position of the fourth fluid inlet 142 with that of the fluid outlet 143 would be unfavorable to the formation of the droplet.

In addition, when the embodiment in FIG. 1 is presented in a 2D manner, i.e. the crossing of the first microchannel 10 and the second microchannel 14 is in a plane, the oil fluid through the falling structure is easy to attach to the wall and flow out of the droplet-generating device along the wall, and thus the oil droplets would hard to be formed.

Hereinafter another exemplary manner of generating the droplets by using the first preferred embodiment is described. The dispersed phase fluid is brought into the first fluid inlet 101 and the second fluid inlet 102 and the continuous phase fluid is brought into the third fluid inlet 141. When the microchannels are made of PDMS, water droplets, but not oil droplets, could be formed between the intersection region 12 and the three-way junction 144 by using this exemplary manner.

Figure 2:
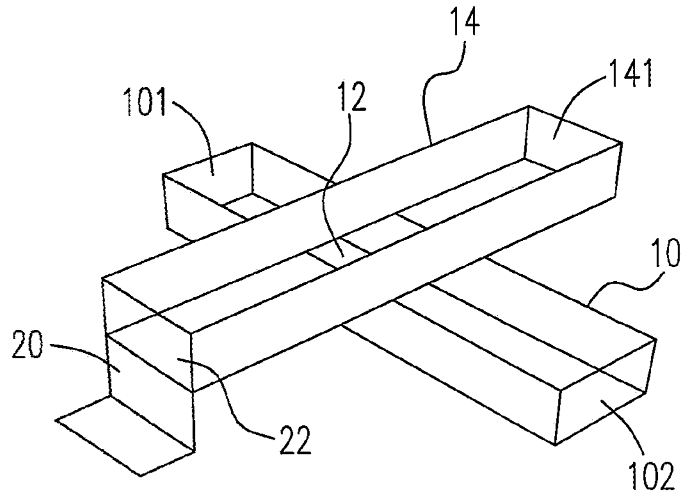
FIG. 2 shows a droplet-generating device according to a second preferred embodiment of the present disclosure.

Please refer to FIG. 2, which is a diagram showing a droplet-generating device according to a second preferred embodiment of the present disclosure. The first microchannel 10 in this embodiment is identical to that in the first preferred embodiment, and the second microchannel 14 in this embodiment includes a third fluid inlet 141 and an outlet 22. The droplet-generating device in FIG. 2 further includes a falling structure 20 connected to the outlet 22. When the dispersed phase fluid is brought into the first fluid inlet 101 and the continuous phase fluid is brought into the second and third fluid inlets 102 and 141, the dispersed phase fluid would flow from the first microchannel 10 to the second microchannel 14 through the intersection region 12, and fall at the falling structure 20 to form the droplets. The height of the falling structure, i.e. the height of the step riser, may be the same with or different from that of the second microchannel 14. The falling structure may be configured by at least a portion of a side wall and at least a portion of a bottom of a third microchannel (not shown) connected to the second microchannel 14.

In various embodiments, the ratio (hereinafter referred to as "R value") of the flow rates of the continuous phase and the dispersed phase is ranged between about 18 and about 3000. For example, in the first preferred embodiment, there are three inlets for the continuous phase (e.g. water), and for each inlet the flow rate may be 0.5 ml/hr, and thus the total flow rate for the continuous phase is 1.5 ml/hr and the R value may be 300. The oil droplets generated under the above condition would have a diameter of 68 μm with a generation frequency of 8 droplets/s. Table 1 shows the size of the droplets (e.g. oil droplets) generated under a fixed flow rate 0.005 ml/hr of the dispersed phase (e.g. the oil flow rate denoted by "Qo") and varied flow rates of the continuous phase (e.g. the water flow rate denoted by "Qw") according to the first or the second preferred embodiment. When the Qw is small, the generated oil droplets have a larger size and a reduced quantity. With the increase of Qw, the size of the droplets decreases, but the droplet quantity relatively increases due to the fixed flow rate of the dispersed phase. When the continuous phase (e.g. water) has a total flow rate of 0.27 ml/hr~16.5 ml/hr, the droplets having a diameter of 9 μm to 92 μm could be steadily generated in the same microchannels with an amount of the generated droplets inversely proportional to the size of the generated droplets due to the fixed flow rate of the dispersed phase. Table 2 shows that under the condition where the continuous phase has a flow rate (e.g. the water flow rate denoted by "Qw") in a range of 0.27-12 ml/hr and the dispersed phase has a flow rate (e.g. the oil flow rate denoted by "Qo") in a range of 0.001-0.015 ml/hr, the droplets having a diameter in a range of 92-12 μm could be generated. Specifically, when the water flow rate is 0.27 ml/h and the oil flow rate is 0.005 ml/h, oil droplets with a diameter of 91 μm could be generated; and when the water flow rate is 16.5 ml/h and the oil flow rate is 0.005 ml/h, oil droplets with a diameter of 9 μm could be generated. That is to say, by using the droplet-generating device according to the present disclosure, it is possible to generate droplets with a 1000-fold difference in the size in the same microchannel design.

TABLE 1

| | Qw(ml/hr) | | | |
|---|---|---|---|---|
| | 0.3 | 3 | 7.5 | 12 |
| Diameter of the oil droplets | 88 μm | 49 μm | 35 μm | 12 μm |

TABLE 2

| | Qo | | | | | | | |
|---|---|---|---|---|---|---|---|---|
| Qw | 0.001 | 0.003 | 0.005 | 0.007 | 0.009 | 0.011 | 0.013 | 0.015 |
| | diameter | | | | | | | |
| 12 | nd | nd | 12 | 12 | 12 | 12 | 13 | 14 |
| 10.5 | nd | nd | 17 | 17 | 17 | 17 | 18 | 18 |
| 9 | nd | 27 | 28 | 28 | 28 | 28 | 28 | 29 |
| 7.5 | nd | 35 | 35 | 35 | 35 | 36 | 36 | 38 |
| 6 | nd | 43 | 45 | 45 | 46 | 45 | 46 | 48 |
| 4.5 | nd | 45 | 47 | 50 | 50 | 53 | 56 | 55 |
| 3 | nd | 46 | 49 | 53 | 60 | 65 | 65 | 68 |
| 1.5 | 49 | 53 | 68 | 73 | 76 | 78 | 78 | 78 |
| 1.2 | 56 | 59 | 71 | 75 | 77 | 78 | 80 | 81 |
| 0.9 | 59 | 64 | 73 | 77 | 79 | 80 | 82 | 82 |
| 0.6 | 61 | 67 | 79 | 82 | 83 | 83 | 85 | 87 |
| 0.3 | 80 | 85 | 88 | 88 | 88 | 90 | 90 | 89 |
| 0.27 | 84 | 88 | 91 | 91 | 92 | 92 | 92 | 92 |

"nd" denotes data not unavailable

In the embodiments of the present disclosure, by using the tangentially cross structure, the size of the oil droplets and the generation frequency thereof could be effectly controlled by controlling the flow rates of the continuous phase (water) and the dispersed phase (oil), and the oil droplets could be generated with a small R value, i.e. a low water/oil ratio, since the microchannel structure forces the dispersed phase (oil) to be in the middle the microchannel and generate oil droplets there.

When it is desired to use the continuous phase and the dispersed phase to form droplets in the microchannels, it is required to reduce the interfacial tension between two phases, increase the stability of the generated droplets, and establish the mechanism such that the formed droplets leave the inner wall of the channel. In the microchannels, one manner to reduce the interfacial tension between two immiscible fluids is the addition of the surfactant into the fluids. The surfactant including those known in this field, such as sodium coceth sulfate (SCS) and the like, may be added, at a concentration of 2-70 wt %, into only the continuous phase fluid or both the continuous phase and the dispersed phase fluids. For example, 2% of SCS may be added into the continuous phase fluid in the first embodiment.

Figure 3A:
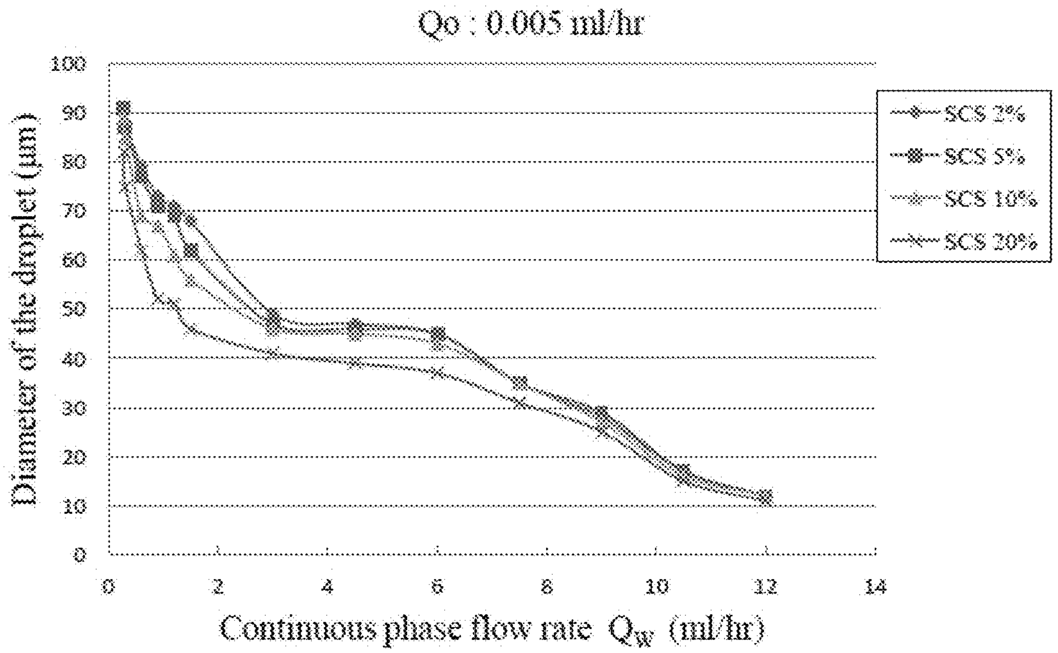
FIGS. 3A and 3B show the effects of different concentrations of the surfactant (SCS) on the droplet size (FIG. 3A) and the droplet generation frequency (FIG. 3B).
Figure 3B:
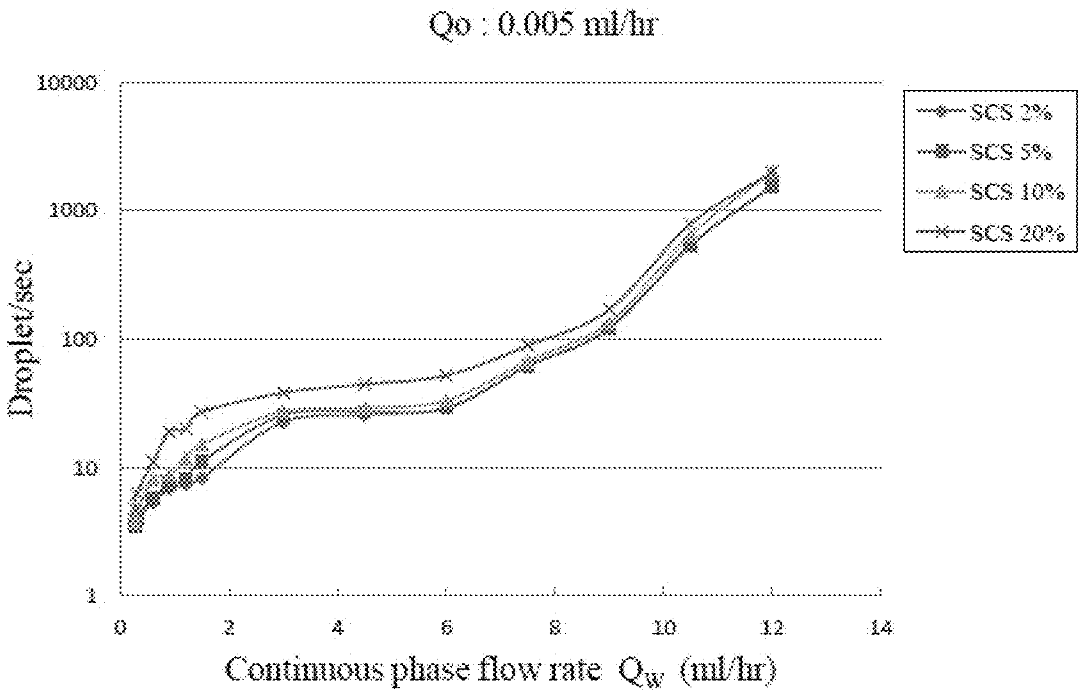

Please refer to FIGS. 3A and 3B, which show the effects of different concentrations of the surfactant (SCS) on the droplet size (FIG. 3A) and the droplet generation frequency (FIG. 3B). FIG. 3A is plotted with the total flow rate Qw (ml/hr) of the continuous phase of water on the X-axis and the corresponding diameter (μm) of the generated droplets on the Y-axis. It could be known from FIGS. 3A and 3B that, at the same flow rate of the continuous phase, with the increased concentration of SCS, the droplet size reduces, and the generation frequency increases due to the fixed flow rate of the dispersed phase (oil). Therefore, the addition of the surfactant may reduce the size of the generated droplets with an increased generation frequency. However, it is found the addition of a small amount of the SCS (e.g. 2%) would not significantly affect the generation of the droplets or the droplet size.

Figure 4A:
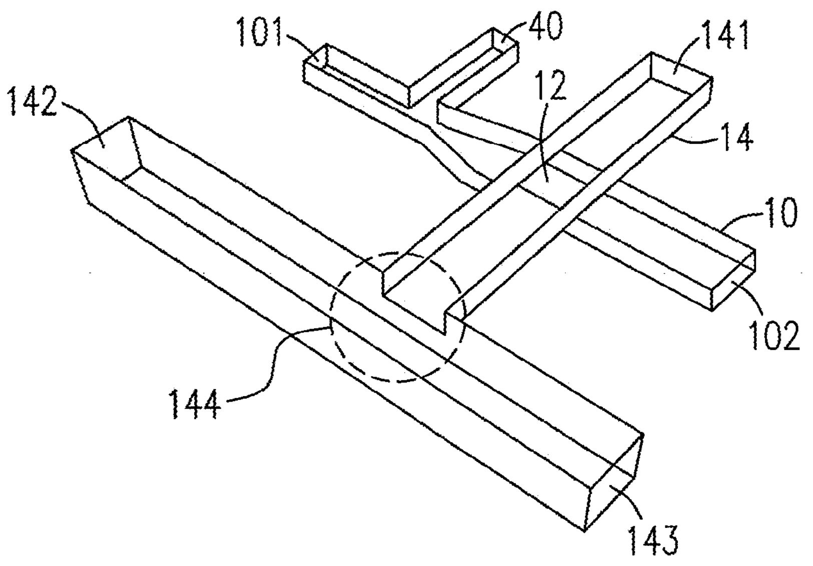
FIG. 4A shows a droplet-generating device according to a third preferred embodiment of the present disclosure.

Please refer to FIG. 4A, which is a diagram showing a droplet-generating device according to a third preferred embodiment of the present disclosure. The main difference between the present embodiment and the first preferred embodiment is that the first microchannel 10 in this embodiment is a 2D T-shaped microchannel. As shown, in addition to the first fluid inlet 101 and the second fluid inlet 102, the first microchannel 10 further comprises a fifth fluid inlet 40. The first microchannel 10 may have different AR values. More specifically, the first microchannel 10 has a constant height and a width different according to the positions. For instance, the first microchannel 10 on the left side of the intersection region 12 may be a T-shaped portion with a width of 50 μm and an AR value of 0.9, which from left to right is gradually extended as a microchannel with a width of 100 μm.

The method of using the droplet-generating device of the third preferred embodiment to generate the droplets may include the manner described hereinafter. A first fluid may be bought into the first fluid inlet 101, and a second fluid immiscible with the first fluid may be brought into the second, third, fourth and fifth fluid inlets 102, 141, 142 and 40. When the first fluid is oil and the second fluid is water, firstly, the shearing force caused by the T-shaped structure would result in the water droplets dispersed in oil in the T-shaped portion of the first microchannel 10. The water droplets then flows from the first microchannel 10 into the second microchannel 14 via the intersection region 12, and are encompassed by the oil by the falling structure at the three-way junction 144 to form water-in-oil-in-water (W/O/W) double emulsion droplets, i.e. water droplets encapsulated in oil shells. In the above embodiment, water could be used as the first fluid and oil could be used as the second fluid for forming the oil-in-water-in-oil (O/W/O) double emulsion droplets as well.

Based on the designed operation principles, the continuous phase may become the dispersed phase in a different portion of the microchannels. Please refer to FIG. 4B where symbols "O" and "W" respectively denote oil and water, and the numbers "1" and "2" following the above symbols respectively denote the working fluids working in a first stage and a second stage. Oil O1 is the continuous phase in the first stage where water droplets are generated and is the dispersed phase and encompassed by the continuous phase of water W2 for forming the oil droplets containing the water droplets in the second stage. The flow rate of W1 may be in a range of 0.003-0.006 ml/hr, the flow rate of O1 may be in a range of 0.001-0.015 ml/hr, and the flow rate of W2 may be in a range of 0.3-3 ml/hr.

Figure 4B:
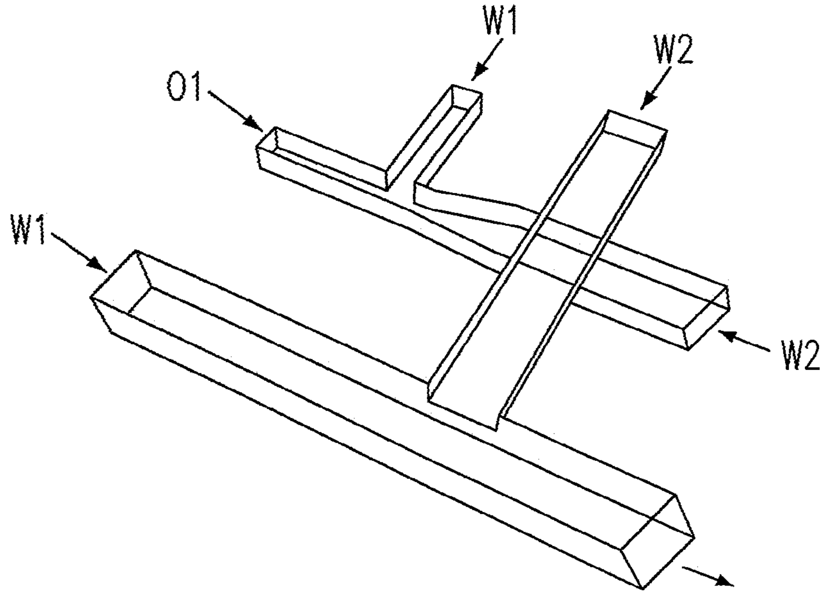
FIG. 4B shows the exemplary manner of using the droplet-generating device of the third preferred embodiment in FIG. 4A to generate droplets.
Figure 5:
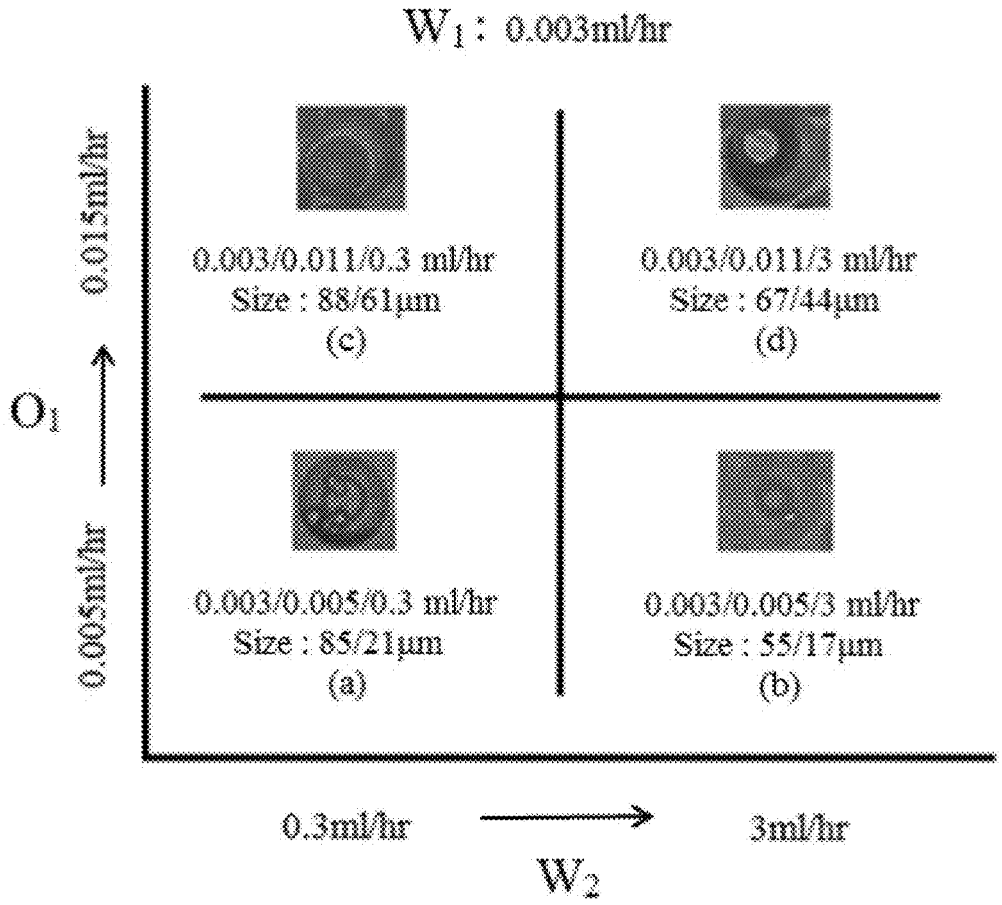
FIG. 5 shows according to the embodiment in FIG. 4B, the effects of different flow rates (ml/hr) of O1 and W2 on the size of the double emulsion droplets under the condition where the flow rate of W1 is fixed to 0.003 ml/hr.

Please refer to FIG. 5, which shows according to the embodiment in FIG. 4B, the effects of different flow rates (ml/hr) of O1 and W2 on the size of the double emulsion droplets under the condition where the flow rate of W1 is fixed to 0.003 ml/hr. As shown in FIG. 5(*a*), when the overall flow rate is small, a number of inner water droplets are small due to the small O1 height. For example, when the flow rates of W1/O1/W2 are 0.003/0.005/0.3 (ml/hr), the size of the water-in-oil (W/O) double emulsion droplets is about 85/21 μm (outer oil droplet diameter/inner water droplet diameter). When W2 is increased as shown in the right lower region, the size of the inner water droplets is further decreased due to a lower height of O1, and the whole droplet size and the number of the inner droplets are decreased as well. For example, when the flow rates of W1/O1/W2 are 0.003/0.005/3 (ml/hr), the size of the water-in-oil (W/O) double emulsion droplets is about 55/17 μm. As shown in FIG. 5(*b*), merely one tiny water droplet is encompassed. While the flow rate of O1 is increased, as shown in the upper region, the size of the inner water droplets is increased due to the increased height of O1. While the flow rate of W2 is increased, as shown from the left upper region to the right upper region, the size of the inner water droplets is smaller due to the somewhat decreased height of O1. For example, when the flow rates of W1/O1/W2 are 0.003/0.011/0.3 (ml/hr), the sizes of the droplets are about 88/61 μm. As shown in FIG. 5(*d*), when the flow rates of W1/O1/W2 are 0.003/0.011/3 (ml/hr), the sizes of the droplets are about 67/44 μm. It could be known from FIGS. 5(*a*)-5(*d*) that in the third preferred embodiment, the size of the inner water droplets and the thickness of the oil shell could be changed by controlling O1, and the whole size of the droplets would be influenced by W2. Therefore, when the third preferred embodiment is used to generate the double emulsion droplets, various patterns could be formed by controlling the flow rates.

Figure 6A:
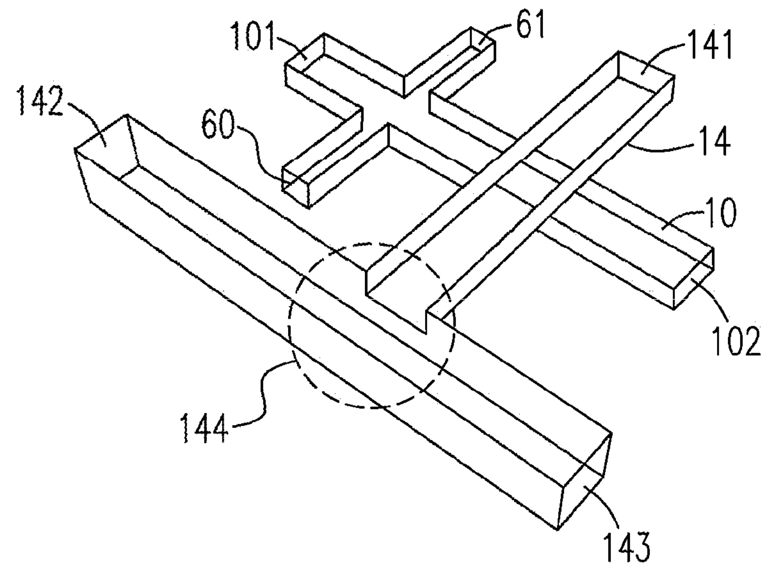
FIG. 6A shows a droplet-generating device according to a fourth preferred embodiment of the present disclosure.

Please refer to FIG. 6A, which is a diagram showing a droplet-generating device according to a fourth preferred embodiment of the present disclosure. The difference between this embodiment and the first preferred embodiment is in this embodiment, the first microchannel 10 is a 2D cross microchannel. As shown, in addition to the first fluid inlet 101 and the second fluid inlet 102, the first microchannel 10 further includes a fifth fluid inlet 60 and a sixth fluid inlet 61.

The fourth preferred embodiment may be practiced in various manners, which may be modified by one skilled in the art by the following examples. For example, a first fluid may be bought into the fifth and sixth fluid inlets 60 and 61, a second fluid immiscible with the first fluid may be bought into the second, the third and the fourth fluid inlets 102, 141 and 142, and a third fluid immiscible with the first fluid may be bought into the first fluid inlet 101. The third fluid may be identical with or different from the second fluid. When the first fluid is oil and the second and third fluids are water, at the cross portion of the first microchannel 10, the dispersed phase (water) is symmetrically pressed by the continuous phase (oil) and thus is separated from the wall of the microchannel and hydrodynamically focused into a narrow stream (i.e. the fluid flow-focusing manner) for forming the water droplets dispersed in the oil. The water droplets moves from the first microchannel 10 to the second microchannel 14 via the intersection region 12 and is encompassed by the oil at the falling structure at the three-way junction 144 so as to form the water-in-oil (W/O) double emulsion droplets dispersed in the water. In the above embodiment, it is also applicable to use the water as the first fluid and the oil as the second and third fluids for forming the oil-in-water (W/O) double emulsion droplets dispersed in the oil.

Alternatively, the first fluid could be brought into the first fluid inlet 101, and the second fluid immiscible with the first fluid could be brought into the second, third, fourth, fifth and the sixth fluid inlets 102, 141, 142, 60, and 61. When the first fluid is oil and the second fluid is water, oil droplets could be formed finally.

Figure 6B:
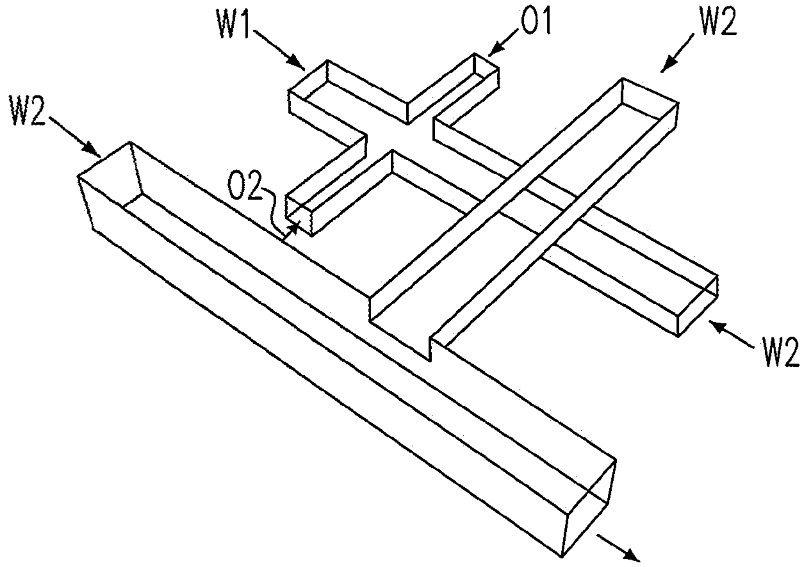
FIG. 6B shows the exemplary manner of using the droplet-generating device of the fourth preferred embodiment in FIG. 6A to generate droplets.

Please refer to FIG. 6B where symbols "O" and "W" respectively denote oil and water, and the numbers "1" and "2" following the above symbols respectively denote the working fluids working in a first stage and a second stage. Oil O1 is the continuous phase in the first stage where water droplets are generated by the aid of W1, and is the dispersed phase and encompassed by the continuous phase of water W2 for forming the oil droplets containing the water droplets in the second stage. For each associated fluid inlets, the flow rate of W1 may be in a range of 0.003-0.08 ml/hr, the flow rate of O1 may be in a range of 0.001-0.16 ml/hr, and the flow rate of W2 may be in a range of 0.3-3 ml/hr. Preferably, the flow rate of W1 may be in a range of 0.007-0.01 ml/hr. The abovementioned ranges of the flow rates are based on the height and width of the microchannels in this embodiment. One skilled in the art could adjust the flow rates of the fluids according to the abovementioned ranges if the height and width of the microchannels change.

Figure 7:
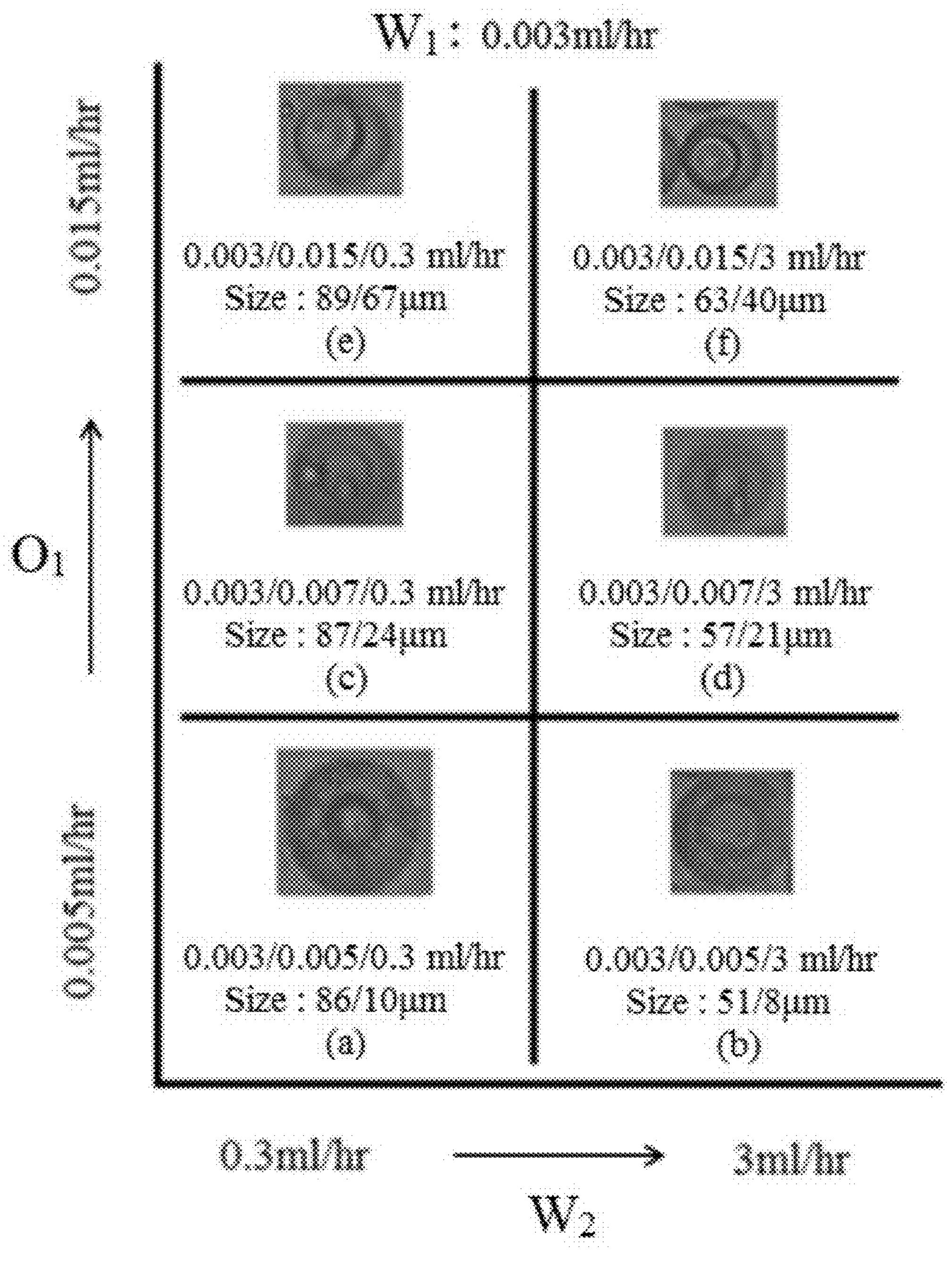
FIG. 7 shows according to the embodiment in FIG. 6B, the effects of different flow rates (ml/hr) of O1 and W2 on the size of the double emulsion droplets under the condition where the flow rate of W1 is fixed to 0.003 ml/hr.

Please refer to FIG. 7, which shows according to the embodiment in FIG. 6B, the effects of different flow rates (ml/hr) of O1 and W2 on the size of the double emulsion droplets under the condition where the flow rate of W1 is fixed to 0.003 ml/hr. As shown in FIG. 7(*a*), when the flow rates of W1/O1/W2 are 0.003/0.005/0.3 (ml/hr), the sizes of the water-in-oil (W/O) double emulsion droplets are about 86/10 μm (oil droplet diameter/water droplet diameter). When the flow rates of W1/O1/W2 are 0.003/0.005/3 (ml/hr), the sizes of the water-in-oil (W/O) double emulsion droplets are about 51/8 μm, as shown in FIG. 7(*b*) where merely two tiny water droplets are contained in an oil droplet. While O1 is increased to 0.007 ml/hr, the size of the water droplets would slightly increase due to the increased height of O1. While W2 is increased in FIG. 7 from left to right, the size of the water droplets is smaller due to the slightly decreased O1 height, as shown in FIG. 7(*c*). When the flow rates of W1/O1/W2 are 0.003/0.007/0.3 (ml/hr), the sizes of the generated droplets are about 87/24 μm. As shown in FIG. 7(*d*), the sizes of the generated droplets with less inner droplets are about 57/21 μm as a result of the flow rates of 0.003/0.007/3 (ml/hr). When O1 is increased to 0.015 ml/hr, it is found, as shown in FIG. 7(*e*), when the flow rates of W1/O1/W2 are 0.003/0.015/0.3 (ml/hr), the generated water droplets not substantially being affected by the 3D cross structure directly pass the intersection region 12 and are encompassed by the oil droplets with the original size of the water droplets at the falling structure, so as to form the double emulsion droplets with sizes of about 89/67 μm. As shown in FIG. 7(*f*), when the flow rates of W1/O1/W2 are 0.003/0.015/3 (ml/hr), the size of the water droplets is decreased as a result of the increased W2, which cause the decreased height of O1, and thereby the whole size of the droplets is diminished to about 63/40 μm. At this case, in order to reduce the effect of the structure on the water droplets generated by W2, O1 should be increased to have an enough height for the passing of the water droplets with the original size. In the region of FIG. 7 where the size of the water droplets is not affected by the 3D cross structure, O1 would be increased as a result of the increased W2. Therefore, the encompassing types that could be achieved by using the fourth preferred embodiment are similar to those by using the third preferred embodiment. That is to say, various encompassing types including the size and the number of the inner droplets and the size of the outer droplets could be formed. Further, in the fourth preferred embodiment, the water droplet diameter generated by W1 is less than 100 μm. The above results also show that in a certain proportion of O1 to W2 and a certain whole flow rate, as those shown in the region of FIG. 7(*e*), the thickness of O1 is enough for the successful pass of the water droplets with the original size without being affected by the microchannel structure, and thus the generation frequency of the water droplets could be directly adjusted by controlling the flow rate of W1.

When O1 is fixed to 0.02 ml/hr and W2 is fixed to 1.5 ml/hr, the flow rate range of about 0.007-0.013 ml/hr of W1 would cause a higher success encompassing rate of the droplets. In detail, when W1 is increased from 0.007 ml/hr to 0.009 ml/hr, the number of the inner droplets that are successfully encompassed is increased. 0.01 ml/hr of W1 shows the best success encompassing rate. Although W1 of a large flow rate (such as that with a flow rate over 0.013 ml/hr) would increase the number and size of the inner water droplets, the high generate frequency would reduce the success rate of the enclosure of the inner droplets. While the ratio of W1 to O1 is about 1:2, a better success rate could be obtained due to a generation frequency of about 1:1 of the water droplets to the oil droplets. When the water droplets are formed without being affected by the structure of the microchannel, the ratio of the whole flow rates of W1/O1/W2 in a range of 1:2:25-150 could result in a better success rate of the enclosure of the inner droplets. A ratio of the flow rates too large or too small may apparently increase the failure rate of encompassing the inner droplets. Table 3 shows the exemplary flow rates (ml/hr) of W1/O1/W2 and the sizes (μm) of the generated water-in-oil (W/O) double emulsion droplets.

TABLE 3

| W1/O1/W2(ml/hr) | oil droplet size/water droplet size (μm) |
|---|---|
| 0.007/0.02/1.5 | 75/61 |
| 0.008/0.02/1.5 | 77/64 |
| 0.009/0.02/1.5 | 77/64 |
| 0.011/0.02/1.5 | 78/66 |
| 0.012/0.02/1.5 | 77/66 |
| 0.01/0.02/1.5 | 77/65 |
| 0.005/0.01/1.5 | 74/64 |
| 0.01/0.02/1.5 | 77/65 |
| 0.02/0.04/1.5 | 84/66 |
| 0.04/0.08/1.5 | 88/67 |
| 0.06/0.12/1.5 | 91/69 |
| 0.08/0.16/1.5 | 90/69 |

For the fourth preferred embodiment, if a gas is brought into the first fluid inlet 101, water is brought into the second, the third and the fourth fluid inlets 102, 141 and 142, and oil is brought into the fifth and sixth fluid inlets 60 and 61, bubbles dispersed in oil could be generated in the first microchannel 10, and the double emulsion droplets, i.e. the oil droplets containing the inner bubbles, could be generated in the second microchannel 14. By the similar way, the double emulsion droplets containing the inner bubbles could be generated by using the third preferred embodiment in FIG. 4A.

Figure 8:
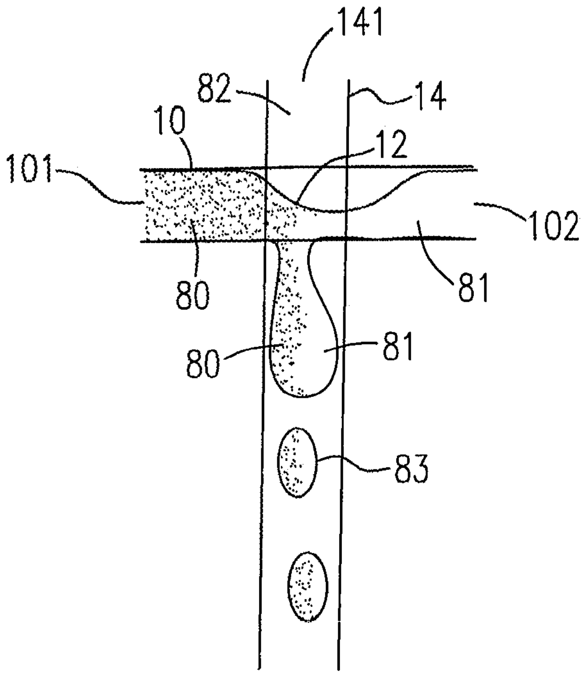
FIG. 8 shows the exemplary manner of generating droplets containing a specific substance according to various embodiments of the present disclosure.

For various embodiments in the present disclosure, a fluid containing a specific substance could be used to generate droplets containing the specific substance. For example, please refer to FIG. 8, which shows the exemplary manner of generating droplets containing the specific substance according to various embodiments of the present disclosure. FIG. 8 simply shows the cross superimposition portion of the first microchannel 10 and the second microchannel 14 in various embodiments. The first dispersed phase fluid (e.g. ink 80 with a concentration of 40%) is brought into the first fluid inlet 101, the second dispersed phase fluid (e.g. water 81) is brought into the second fluid inlet 102, and the continuous phase fluid (e.g. oil 82) is brought into the third fluid inlet 141. Then, the ink 80 meets the water 81 and flows from the first microchannel 10 to the second microchannel 14 at the intersection region 12. Consequently, the mixed water droplets 83 containing the ink 80 and water 81 and dispersed in the oil 82 are generated. In the above method, when the R value is 2, the mixed droplets with a higher stability could be generated. If the R value is fixed, the concentration of the substance in the droplets could be controlled by adjusting the flow rates of the two dispersed phases. For example, when the flow rate of the continuous phase fluid is 0.5 μl/min, that of the dispersed phase fluid is 0.25 μl/min, which contains the water flow rate of 0.15 μl/min and the 40% ink flow rate of 0.1 μl/min, and the R value is 2, the mixed water droplets 83 with a concentration of 16% could be generated. For the cases where the mixed water droplets 83 have a concentration of 8% or 32%, since the flow rate of the ink 80 or water 81 is too large, the intrusion into the microchannels of the other phase at the intersection window may occurs. The mixed droplets with a concentration in a range of 16%-24% are more stable during the generation thereof.

Figure 9:
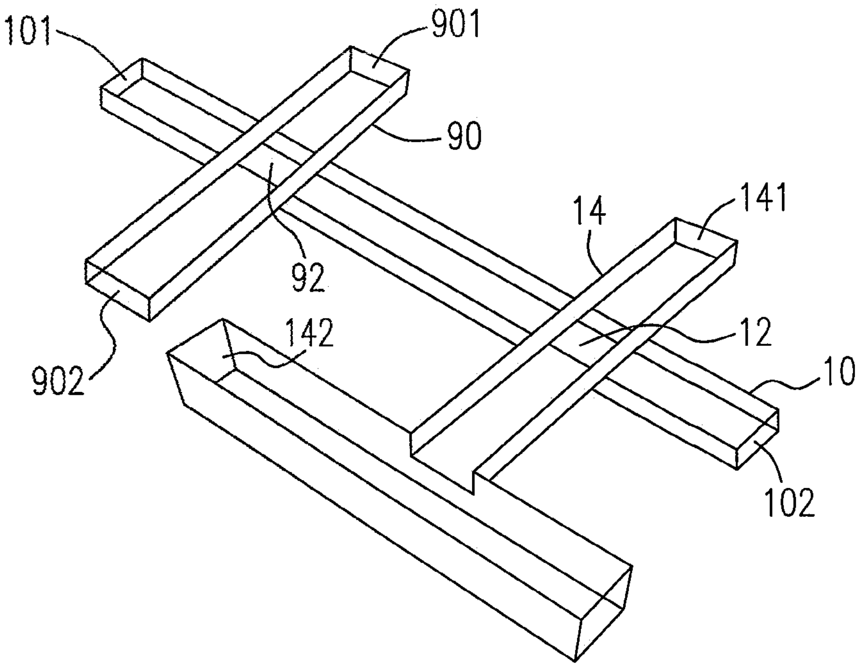
FIG. 9 shows a droplet-generating device according to a fifth preferred embodiment of the present disclosure.

Please refer to FIG. 9, which is a diagram showing a droplet-generating device according to a fifth preferred embodiment of the present disclosure. Compared with the first preferred embodiment, the difference is that this embodiment further includes a third microchannel 90 superimposed on the first microchannel 10 to form a further intersection region 92, through which the third microchannel 90 is in communication with the first microchannel 10. The third microchannel 90 is superimposed on and crossing the first microchannel 10 at a perpendicular angle or other angles. As shown, the third microchannel 90 includes a fifth fluid inlet 901 and a sixth fluid inlet 902. However, based on the actual demand, the third microchannel 90 could merely further include a fifth fluid inlet 901.

The exemplary manner for generating droplets by using the fifth preferred embodiment is described as follows. Oil is brought into the first fluid inlet 101, an aqueous compound solution is brought into the fifth fluid inlet 901, and an aqueous drug solution is brought into the sixth fluid inlet. Then, mixed water droplets dispersed in the oil are formed between the intersection region 12 and the further intersection region 92, wherein the mixed water droplets containing the compound and the drug. The concentrations of the compound and the drug in the mixed water droplets could be adjusted by controlling the flow rates of the compound solution and the drug solution. Further, water is directed into the second, the third and the fourth fluid inlets 102, 141 and 142, and consequently the double emulsion droplets where the mixed water droplets are encompassed by the oil droplets are generated. The above embodiment is advantageous in the proceedings of the chemical reactions or the reactive test for the drugs and the compounds. Further, the reaction product could be protected in the droplets, particularly the oil droplets, for the subsequent conveyance or storage.

The droplet-generating device of various embodiments in the present disclosure could be fabricated by the photolithography, which has been commonly applied to the fabrication of the microchannels, or other technologies well-known in this field. If not specified, the width and the AR value of the microchannels of various embodiments in the present disclosure are 100 μm and 0.45, respectively, and the resulting droplets may have a diameter in a range of 9-92 μm. However, based on the actual demand for, e.g. the desired droplet size, the width of the microchannel could be tens of micrometers (or less) to hundreds of micrometers (or more), and the AR value may be in a range of 0.3-3, wherein preferably, the AR value is less than 1. The materials for fabricating the microchannel in various embodiments could be PDMS, glass, plastics, or any material suitable for the photolithography process. Further, one skilled in the art could appreciate that the microchannel made of the hydrophobic materials is conducive to the formation of the water droplets, and the microchannel made of the hydrophilic materials is conducive to the formation of the oil droplets. However, for the 3D droplet-generating device according to the present invention, it is possible to generate the oil droplets rapidly and steadily by using the hydrophobic microchannel (e.g. the PDMS microchannel), and vice versa.

The various embodiments in the present disclosure are based on the basic channels, such as 2D-T shaped, 2D-cross shaped, 3D-T shaped, 3D-cross shaped channels or the combination thereof. Based on the knowledge of the above basic channels of one skilled in the art in combination of the above descriptions, particularly those for generating the droplets by using the first preferred embodiment, it is easy for one skilled in the art to conceive other embodiments for generating the droplets by using the droplet-generating device of the present disclosure, which all fall in the protecting scopes of the present disclosure. It is not easy to form the oil droplets by using the channels made of the PDMS. Namely, it is not necessary that the well-known manner for generating the water droplets could be used to generate the oil droplets. Therefore, most examples in the present disclosure are given for generating the oil droplets. However, the examples are not best or optimal, and the device and method disclosed in the present disclosure could be used to generate the water droplets, as well. Further, if the droplet-generating device of the present disclosure is used to generate water droplets, based on the common knowledge in this field, there would be more embodiments could be utilized without departing from the scope of the invention.

Generally, the channel devices capable of forming the three-dimensional flow-focusing field are complex. However, the droplet-generating device of the present disclosure could form the three-dimensional flow-focusing field by the combination of the basic channels and could form the droplets accordingly. The droplet-generating device of the present disclosure has the advantage in the size range of the formed droplets over the typical 2D-T shaped or cross-shaped channels. That is to say, the droplet-generating device of the present disclosure could generate droplets with a size difference of about 1000-fold without the requirement of changing the channels. Further, by the combination of the basic channels, the present application could achieve the purpose of generating the double emulsion droplets without changing the properties of the encompassed phase. Since the devices of the present disclosure could generate droplets with a size of mere 9 μm, the double emulsion droplets could be applied to the reaction of minute samples. This new microfluidic device can be promising for a variety of applications such as emulsification, nano-medicine and droplet-based microfluidics.

Some embodiments of the present disclosure are described in the followings.

1. A droplet-generating device comprises: a first microchannel including a first fluid inlet and a second fluid inlet; and a second microchannel crossing over and communicating with the first microchannel at an intersectional region, wherein the second microchannel includes a third fluid inlet, a fourth fluid inlet, a fluid outlet, a three-way junction and a side wall, the intersectional region is configured between the third fluid inlet and the three-way junction, and the side wall is disposed between the fourth fluid inlet and the fluid outlet and extended downward.

2. A droplet-generating device of Embodiment 1, wherein the first fluid inlet is a dispersed phase fluid inlet, and each of the second, the third and the fourth fluid inlets is a continuous phase fluid inlet.

3. A droplet-generating device of any one of the above Embodiments, wherein:

the first microchannel further includes a fifth fluid inlet and a sixth fluid inlet, both of the fifth fluid inlet and the first fluid inlet are configured between the sixth fluid inlet and the intersectional region, and the first and the fifth fluid inlets are configured for inletting a first fluid, and the second, the third and the fourth fluid inlets are configured for inletting a second fluid being immiscible with the first fluid for generating a microdroplet between the sixth fluid inlet and the intersectional region.

4. A droplet-generating device of any of the above Embodiments, wherein the sixth fluid inlet is configured for inletting one of the second fluid and a third fluid being immiscible with the first fluid.

5. A droplet-generating device of any of the above Embodiments, wherein:

the first microchannel further includes a fifth fluid inlet and a sixth fluid inlet, the fifth fluid inlet and the first fluid inlet are configured between the sixth fluid inlet and the intersectional region, and each of the first, the second, the third, the fourth and the fifth fluid inlets is configured for inletting a first fluid, and the sixth fluid inlet is configured for inletting a second fluid being immiscible with the first fluid for generating a microdroplet between the sixth fluid inlet and the intersectional region.

6. A droplet-generating device of any of the above Embodiments, wherein the first microchannel further includes a fifth fluid inlet configured between the first fluid inlet and the intersectional region, the second, the third, the fourth and the fifth fluid inlets are configured for inletting a first fluid, and the first fluid inlet is configured for inletting a second fluid being immiscible with the first fluid so as to form a microdroplet between the first fluid inlet and the intersectional region.

7. A droplet-generating device of any of the above Embodiments further comprises a third microchannel crossing over and communicating with the first microchannel at a second intersectional region configured between the intersectional region and the first fluid inlet, wherein the third microchannel includes a fifth fluid inlet, the second, the third, the fourth and the fifth fluid inlets are configured for inletting a first fluid, and the first fluid inlet is configured for inletting a second fluid being immiscible with the first fluid for generating a microdroplet between the intersectional region and the second intersectional region.

8. A droplet-generating device of any of the above Embodiments further comprises a third microchannel crossing over and communicating with the first microchannel at a second intersectional region configured between the intersectional region and the first fluid inlet, wherein the third microchannel includes a fifth fluid inlet and a sixth fluid inlet, the second, the third, the fourth, the fifth and the sixth fluid inlets are configured for inletting a first fluid, the first fluid inlet is configured for inletting a second fluid being immiscible with the first fluid for generating a droplet at the three-way junction and generating a microdroplet between the intersectional region and the second intersectional region, and the microdroplet is contained in the generated droplet.

9. A droplet-generating device of any of the above Embodiments, wherein the second microchannel is one of a T-shaped microchannel and a Y-shaped microchannel.

10. A droplet-generating device comprises: a first channel including a first inlet and a second inlet; a second channel crossing over and communicating with the first channel and including a third inlet and a first outlet; and a falling structure connected with the first outlet.

11. A droplet-generating device of any of the above Embodiments further comprises a third microchannel connected with the first outlet of the second channel at a three-way intersectional part and including a fourth inlet and a second outlet.

12. A droplet-generating device of any of the above Embodiments, wherein the third channel includes a side wall and a bottom, and the falling structure is configured by at least a portion of the side wall and at least a portion of the bottom.

13. A droplet-generating device of any of the above Embodiments, wherein each of the first channel, the second channel and the third channel has a height and a width, and at least one of the first channel, the second channel and the third channel has a ratio of a height to a width in a range of 0.3-3.

14. A method of producing a droplet comprises steps of providing a first channel including a first inlet and a second inlet; providing a second channel crossing over and communicating with the first channel and including a third inlet and an outlet; providing a falling structure connected to the outlet; introducing a first flowing material through the first inlet into the first channel; and introducing a second flowing material through the second inlet and the third inlet into the first channel and the second channel respectively so as to produce the droplet at the falling structure.

15. A method of Embodiment 14, wherein the first flowing material is a dispersed phase fluid and the second flowing material is a continuous phase fluid.

16. A method of any of the Embodiments 14-15 further comprises a step of adding a drug into at least one of the first flowing material and the second flowing material, wherein the droplet has a size of 9~92 μm.

17. A method of any of the Embodiments 14-16, wherein the first flowing material is introduced into the first channel at a first flow rate of 0.001~0.015 mL/hr, and the second flowing material is introduced into the second channel at a second flow rate of 0.27~16.5 mL/hr.

18. A method of any of the Embodiments 14-17, wherein the first flowing material and the second flowing material have a first flow rate and a second flow rate respectively, and a ratio of the second flow rate to the first flow rate is ranged from 18:1 to 3000:1.

19. A method of any of the Embodiments 14-18, wherein the first channel, the second channel and the falling structure are configured as a droplet-generating device, the droplet-generating device further comprises an intersectional region and a third channel connected with the outlet of the second channel at a three-way intersectional part and including a fourth inlet, an outlet, a side wall and a bottom, the first channel and the second channel cross at the intersectional region, the falling structure includes a portion of the side wall and a portion of the bottom, the first channel further includes a fifth inlet between the first inlet and the intersectional region, and the method further comprises steps of introducing the second flowing material through the fourth inlet into the second channel; and introducing the second flowing material through the fifth inlet into the first channel so as to generate a droplet between the first inlet and the intersectional region.

20. A method of any of the Embodiments 14-19, wherein the first channel and the second channel cross at the intersectional region, the first channel further includes a fifth inlet and a sixth inlet, the fifth inlet and the first inlet are configured between the sixth inlet and the intersectional region, and the method further comprises steps of: introducing the first flowing material through the first and the fifth inlets into the first channel; and introducing the second flowing material through the sixth inlet into the first channel so as to generate a droplet between the sixth inlet and the intersectional region.

While the invention has been described in terms of what is presently considered to be the most practical and preferred embodiments, it is to be understood that the invention needs not be limited to the disclose embodiments. Therefore, it is intended to cover various modifications and similar arrangements included within the spirit and scope of the appended claims, which are to be accorded with the broadest interpretation so as to encompass all such modifications and similar structures.

What is claimed is:

1. A droplet-generating device, comprising:

a first microchannel including a first fluid inlet and a second fluid inlet; and a second microchannel crossing over and communicating with the first microchannel at an intersectional region, wherein the second microchannel includes a third fluid inlet, a fourth fluid inlet, a fluid outlet, a three-way junction and a side wall, the intersectional region is configured between the third fluid inlet and the three-way junction, and the side wall is disposed between the fourth fluid inlet and the fluid outlet and extended downward.

2. A droplet-generating device of claim 1, wherein the first fluid inlet is a dispersed phase fluid inlet, and each of the second, the third and the fourth fluid inlets is a continuous phase fluid inlet.

3. A droplet-generating device of claim 1, wherein:

the first microchannel further includes a fifth fluid inlet and a sixth fluid inlet, both of the fifth fluid inlet and the first fluid inlet are configured between the sixth fluid inlet and the intersectional region, and the first and the fifth fluid inlets are configured for inletting a first fluid, and the second, the third and the fourth fluid inlets are configured for inletting a second fluid being immiscible with the first fluid for generating a microdroplet between the sixth fluid inlet and the intersectional region.

4. A droplet-generating device of claim 3, wherein the sixth fluid inlet is configured for inletting one of the second fluid and a third fluid being immiscible with the first fluid.

5. A droplet-generating device of claim 1, wherein:

the first microchannel further includes a fifth fluid inlet and a sixth fluid inlet, the fifth fluid inlet and the first fluid inlet are configured between the sixth fluid inlet and the intersectional region, and each of the first, the second, the third, the fourth and the fifth fluid inlets is configured for inletting a first fluid, and the sixth fluid inlet is configured for inletting a second fluid being immiscible with the first fluid for generating a microdroplet between the sixth fluid inlet and the intersectional region.

6. A droplet-generating device of claim 1, wherein the first microchannel further includes a fifth fluid inlet configured between the first fluid inlet and the intersectional region, the second, the third, the fourth and the fifth fluid inlets are configured for inletting a first fluid, and the first fluid inlet is configured for inletting a second fluid being immiscible with the first fluid so as to form a microdroplet between the first fluid inlet and the intersectional region.

7. A droplet-generating device of claim 1, further comprising:

a third microchannel crossing over and communicating with the first microchannel at a second intersectional region configured between the intersectional region and the first fluid inlet, wherein the third microchannel includes a fifth fluid inlet, the second, the third, the fourth and the fifth fluid inlets are configured for inletting a first fluid, and the first fluid inlet is configured for inletting a second fluid being immiscible with the first fluid for generating a microdroplet between the intersectional region and the second intersectional region.

8. A droplet-generating device of claim 1, further comprising:

a third microchannel crossing over and communicating with the first microchannel at a second intersectional region configured between the intersectional region and the first fluid inlet, wherein the third microchannel includes a fifth fluid inlet and a sixth fluid inlet, the second, the third, the fourth, the fifth and the sixth fluid inlets are configured for inletting a first fluid, the first fluid inlet is configured for inletting a second fluid being immiscible with the first fluid for generating a droplet at the three-way junction and generating a microdroplet between the intersectional region and the second intersectional region, and the microdroplet is contained in the generated droplet.

9. A droplet-generating device of claim 1, wherein the second microchannel is one of a T-shaped microchannel and a Y-shaped microchannel.

* * * * *